United States Patent [19]
Hanai et al.

[11] Patent Number: 5,952,472
[45] Date of Patent: *Sep. 14, 1999

[54] ANTI-FIBROBLAST GROWTH FACTOR-8 MONOCLONAL ANTIBODY

[75] Inventors: Nobuo Hanai, Kanagawa; Motoo Yamasaki; Akiko Furuya, both of Toyko; Akira Tanaka, Tochigi, all of Japan

[73] Assignee: Kyowa Hakko Kogyo Co., Ltd., Japan

[*] Notice: This patent issued on a continued prosecution application filed under 37 CFR 1.53(d), and is subject to the twenty year patent term provisions of 35 U.S.C. 154(a)(2).

[21] Appl. No.: 08/832,236

[22] Filed: Apr. 3, 1997

[30] Foreign Application Priority Data

Apr. 3, 1996 [JP] Japan ................................ 8-081754

[51] Int. Cl.⁶ .............................. C07K 16/00; C12N 5/06
[52] U.S. Cl. ..................................... 530/387.1; 530/387.9; 530/388.1; 530/388.2; 530/388.23; 530/388.85; 530/387.7; 435/326
[58] Field of Search ............................. 530/387.1, 387.9, 530/387.7, 388.2, 388.23, 388.85; 435/7.1, 326

[56] References Cited

FOREIGN PATENT DOCUMENTS 9503831  2/1995  WIPO .

OTHER PUBLICATIONS

Prac. Natl. Acad. Sci. USA, vol. 89, pp. 8928–8932, Oct. 1992, Biochemistry, "Cloning and characterization of an androgen–induced growth factor essential for the androgen–dependent growth of mouse mammary carcinoma cells", Tanaka et al.

FEBS Letters 3663 (1995) 226–230, Federation of European Biochemical Societies, "Human androgen–induced growth factor in prostate and breast cancer cells: its molecular cloning and growth properties", Tanaka et al.

MacArthur et al. 1995 Cell Growth & Differ Entition vol. 6:817–825.

*Essential Immunology* Blackwell Scientific Publications Oxford England pp. 107–109.

Primary Examiner—Paula K. Hutzell
Assistant Examiner—Susan Ungar
Attorney, Agent, or Firm—Nixon & Vanderhye

[57] ABSTRACT

Described is a monoclonal antibody capable of specifically binding to fibroblast growth factor-8 (FGF-8) which is related to growth factors of hormone-dependent tumor cells such as prostatic cancer and breast cancer, and inhibits the FGF-8 activity. The monoclonal antibody is useful in analyzing the role and biological function of FGF-8 in hormone-dependent tumor cells such as prostatic cancer and breast cancer and can be beneficial in the treatment of these cancers.

3 Claims, 4 Drawing Sheets

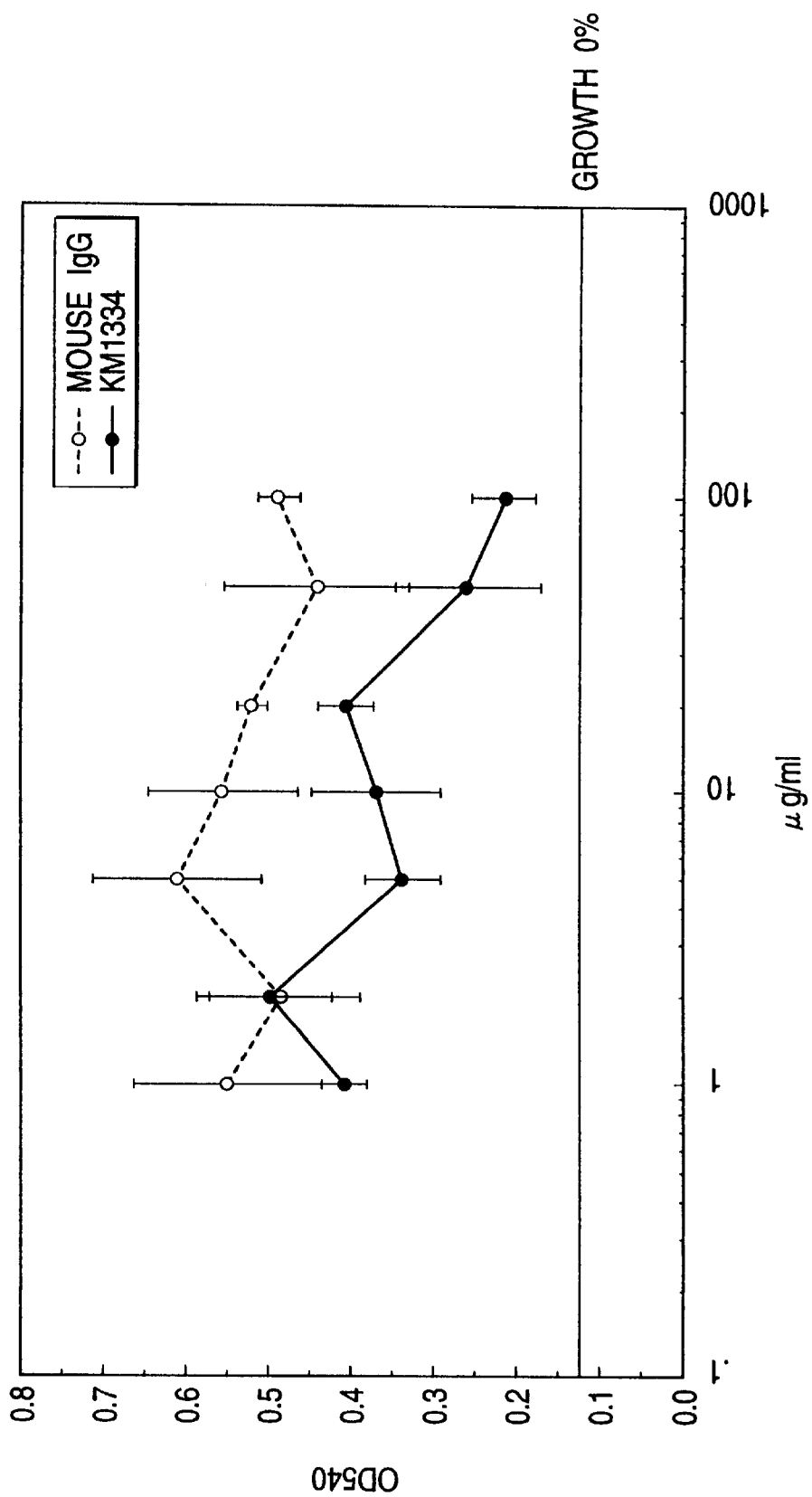

ANTI-FIBROBLAST GROWTH FACTOR-8 MONOCLONAL ANTIBODY

FIELD OF THE INVENTION

The present invention relates to a monoclonal antibody which specifically binds to fibroblast growth factor-8, has a neutralization activity, namely it inhibits activity of fibroblast growth factor-8, and therefore is useful for the morbid state analysis and treatment of human tumor cells grown through induction by fibroblast growth factor-8.

BACKGROUND OF THE INVENTION

Androgen induced growth factor (AIGF) is a factor isolated in 1992 from a culture supernatant of a mouse mammary tumor cell line SC-3 [(Shionogi Carcinoma-3: *J. Steroid Biochem.*, 27, 459 (1987)] which shows sex hormone-dependent growth. AIGF is a growth factor which is induced and produced by androgen stimulation and activates growth of SC-3 cells in an autocrine manner [*Proc. Natl. Acad. Sci.*, 89, 8928–8932, (1992)]. The results of gene cloning efforts revealed that it has a homology of 30 to 40% with the FGF family at the amino acid level, and it was named fibroblast growth factor-8 (hereinafter referred to as "FGF-8"). Thereafter, human FGF-8 was cloned from a human placenta genomic library using mouse FGF-8 as a probe, which coincided with the mouse FGF-8 by a factor of 85% at the nucleotide level and 100% at the amino acid level [*FEBS Letters*, 363, 226 (1995)]. It has been assumed that sex hormone induced growth factors would exhibit an autocrine role in tumors such as prostatic cancer, and breast cancer which show sex hormone-dependent growth, and the isolation and cloning of FGF-8, though in a mouse system, was the first evidence of such a mechanism. It is probable that FGF-8 also plays a role in carcinogenesis and tumor growth in humans by a similar mechanism, but clear evidence has not yet been obtained. However, since expression of FGF-8 m-RNA can be found in several human tumor cell lines of prostatic cancer and breast cancer and enhancement of cell growth can be observed when FGF-8 expressed in CHO cells is added to the culture system of these cell lines or a cell line of fibroblasts [*FEBS Letters*, 363, 226 (1995)], it is highly possible that FGF-8 is one of the growth factors which act on sex hormone-dependent tumors in an autocrine or paracrine manner.

In consequence, an antibody specific for FGF-8 is useful for the analysis of the role and biological function of FGF-8 in the above-mentioned tumor cells, and also for the diagnosis of prostatic cancer, breast cancer and the like by immunological detection. Also, it appears that the antibody having a neutralization activity would be useful in studying biological activities of FGF-8 and effective in treating the cancers.

To date the isolation of a monoclonal antibody specific for FGF-8 has not been reported.

SUMMARY OF THE INVENTION

An object of the present invention is to provide a monoclonal antibody which specifically binds to FGF-8 and inhibits the activity of FGF-8 that has a possibility of being a growth factor of hormone-dependent tumors such as prostatic cancer and breast cancer.

The inventors of the present invention have obtained a monoclonal antibody by preparing hybridomas using a partial peptide of FGF-8 as the immunogen, establishing a hybridoma strain capable of producing a monoclonal antibody which specifically binds to the peptide, culturing the hybridoma in a medium or administering it to an animal to induce an ascites tumor and then collecting the resulting culture supernatant or ascitic fluid. A Western blotting test using the monoclonal antibody confirmed that the antibody can bind to FGF-8 protein, when the monoclonal antibody was added to a culture broth of a mouse mammary tumor cell line SC-3 capable of showing sex hormone-dependent growth, and confirmed that the monoclonal antibody can inhibit the FGF-8 activity, namely it neutralizes FGF-8.

These and other objects of the present invention have been attained by a monoclonal antibody which specifically binds to FGF-8 and inhibits FGF-8 activity.

BRIEF DESCRIPTION OF THE DRAWINGS

FIG. 5 shows the effect of anti-FGF-8 monoclonal antibody KM 1334 in inhibiting the activity of testosterone. In the drawing, the line of growth at 0% indicates a value when neither the growth factor nor antibody were added. The dotted line indicates activity inhibition by purified mouse IgG used as a control antibody, and the solid line by anti-FGF-8 monoclonal antibody KM 1334.

DETAILED DESCRIPTION OF THE INVENTION

Figure 1:
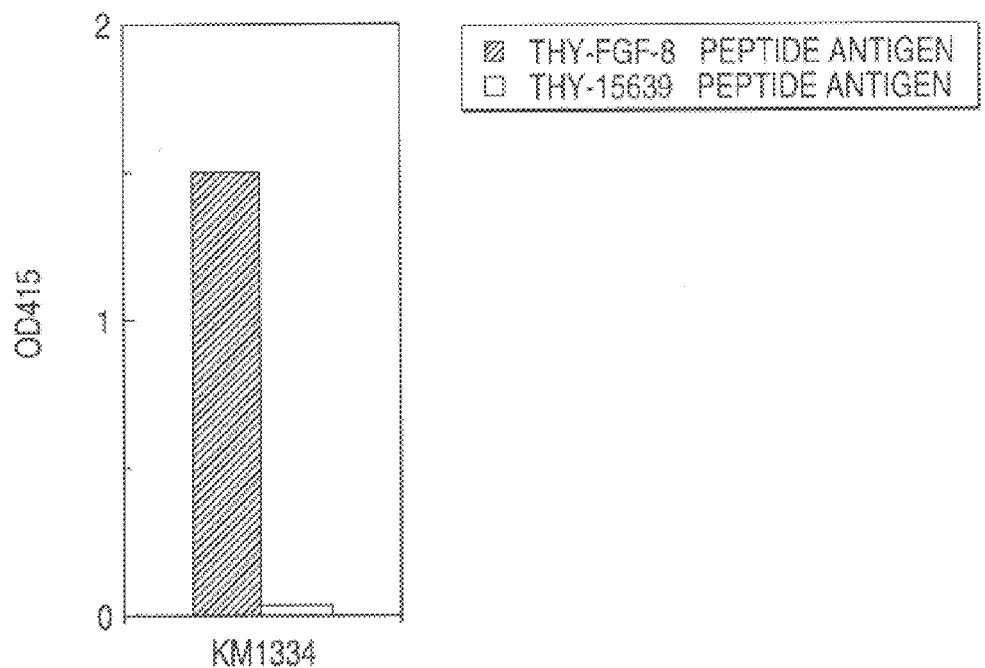
FIG. 1 shows the bindability of anti-FGF-8 monoclonal antibody KM 1334 for antigens in an enzyme immunoassay (the term "anti-FGF-8 monoclonal antibody" as used herein means monoclonal antibody which specifically binds to FGF-8). In the drawing, the black quadrangle indicates the bindability for THY-FGF-8 (hereinafter referred to as "THY") peptide antigen, and the white quadrangle for THY-15639 peptide antigen.

Monoclonal antibody KM 1334 produced by a hybridoma cell line KM 1334 (FERM BP-5451), a monoclonal antibody of the present invention, specifically binds to FGF-8.

(1) Preparation of antigen

As the antigen necessary for the preparation of the anti-FGF-8 monoclonal antibody, FGF-8 producing cells or a cell fraction thereof, or host cells transformed with a DNA fragment which encodes FGF-8, prepared using known techniques by integrating complete or a partial fragment of cDNA which encodes FGF-8 into procaryotic cells (e.g., *Escherichia coli* or the like) or eucaryotic cells (e.g., insect cells, mammal cells or the like) can be used as such or as a protein expressed and purified as a fusion protein, as well as a partial peptide of FGF-8 synthesized using a peptide synthesizer.

In order to increase immunogenicity, the peptide to be used as the antigen is linked to a carrier protein using a cross-linking agent. Examples of the carrier protein include keyhole limpet hemocyanin (hereinafter referred to as "KLH"), bovine serum albumin (hereinafter referred to as "BSA"), cycloglobulin and the like. Examples of the cross-linking agent include glutaraldehyde, N-(m-maleimidobenzoyloxy)succinimide (hereinafter referred to as "MBS") and the like.

(2) Immunization of animal and preparation of antibody-producing cells

Animals immunized are not particularly limited as long as a hybridoma can be prepared. Hereinafter, mice and rats are enumerated as specific examples in the present invention.

Mice or rats of 3 to 20 weeks of age are immunized with the antigen prepared by the method of (1), and antibody-producing cells are collected from the spleen, lymph node or peripheral blood of the immunized animal. The immunization is carried out by administering the antigen together with an appropriate adjuvant (for example, complete Freund's adjuvant or a combination of aluminum hydroxide gel with pertussis vaccine) to the animal subcutaneously, intravenously or intraperitoneally. Following the first administration, the antigen is administered repeatedly 5 to 10 times at intervals of 1 to 2 weeks. Three to 7 days after each administration, a blood sample is collected from the venous plexus of the fundus of the eye, and the serum derived from the sample blood is tested, for example, by enzyme immunoassay [Enzyme-linked Immunosorbent Assay (ELISA), published by Igaku Shoin, 1976] to determine whether it binds to the antigen. A mouse or rat whose serum shows a sufficient antibody titer against the peptide used for immunization is submitted for use as a source of antibody-producing cells. For submission to fusion between splenocytes and myeloma cells, the spleen of the immunized mouse or rat is excised 3 to 7 days after the final administration of the antigenic substance and splenocytes of the spleen are collected. The spleen is cut to pieces in a serum-free basal medium (hereinafter referred to as "washing medium") and centrifuged, and the recovered cells are treated with Tris-ammonium chloride buffer (pH 7.65) for 1 to 2 minutes to eliminate erythrocytes. The remaining cells are then washed with the washing medium and used as splenocytes for cell fusion.

(3) Preparation of myeloma cells

Mouse-derived established cell lines are used as the myeloma cells. Thus, for instance, the 8-azaguanine-resistant mouse (BALB/c-derived) myeloma cell lines P3-X63Ag8-U1 (P3-U1) [Current Topics in Microbiology and Immunology-1; *European Journal of Immunology*, 6, 511–519 (1976)], SP2/O-Ag14 (SP-2) [*Nature*, 276, 269–270 (1978)], P3-X63-Ag8653 (653) [*Journal of Immunology*, 123, 1548–1550 (1979)] and P3-X63-Ag8 (X63) [*Nature*, 256, 495–497 (1975)] may be used. These cell lines are subcultured in an 8-azaguanine medium [prepared by supplementing RPMI-1640 medium with glutamine (1.5 mM), 2-mercaptoethanol ($5 \times 10^{-5}$ M), gentamicin (10 $\mu$g/ml) and fetal calf serum (FCS) (10%) and further supplementing the resulting medium (hereinafter referred to as "normal medium") with 8-azaguanine (15 $\mu$g/ml)]. Three to four days before cell fusion, subculture is performed in the normal medium to thereby ensure a cell number of not less than $2 \times 10^7$ cells on the day of cell fusion.

(4) Cell fusion

The antibody-producing cells obtained as described in (2) and the myeloma cells obtained as described in (3) are respectively washed thoroughly with the washing medium or PBS (1.83 g of disodium phosphate, 0.21 g of monopotassium phosphate and 7.65 g of sodium chloride per liter of distilled water, pH 7.2), and mixed in a proportion of 5 to 10 antibody-producing cells per myeloma cell. After recovering of the cells by centrifugation, the cells are thoroughly loosened, a mixture of 2 g of polyethylene glycol-1,000 (PEG-1,000), 2 ml of the washing medium and 0.7 ml of dimethyl sulfoxide is added to the cells with stirring in an amount of 0.2 to 1 ml/$10^8$ antibody-producing cells at 37° C., then several 1 to 2 ml portions of the washing medium are added at 1- to 2-minute intervals, and the whole amount is made 50 ml by further washing. After centrifugation, the recovered cells are loosened gently and then suspended in 100 ml of HAT medium (prepared by supplementing the normal medium with hypoxanthine ($10^{-4}$ M), thymidine ($1.5 \times 10^{-5}$ M) and aminopterin ($4 \times 10^{-7}$ M)). This suspension is distributed in 100 $\mu$l portions into each well of 96-well culture plates, and incubation is carried out in a 5% $CO_2$ incubator at 37° C. for 7 to 14 days. After incubation, a portion of the culture supernatant is taken from each well and subjected, for example, to enzyme immunoassay which will be described later in (5) or to FACS (fluorescence-activated cell sorter), thereby selecting an antibody which specifically binds to the FGF-8 partial peptide. Thereafter, cloning is repeated twice by the limiting dilution method [using HT medium (HAT medium minus aminopterin) for the first cloning and the normal medium for the second). Cell lines for which a high antibody titer is constantly observed are selected as anti-FGF-8 monoclonal antibody-producing hybridoma cell lines.

(5) Selection of anti-FGF-8 monoclonal antibody

Examples of the enzyme immunoassay for measuring antibodies include the sandwich method, an immunoenzymatic technique, a solid phase method in which an enzyme-labeled second antibody is used, a method in which an immobilized second antibody is used and a solid phase method in which an enzyme/anti-enzyme antibody system is used [*Protein, Nucleic Acid and Enzyme*, Supplement No.31, p.23 (1987)]. The following describes the method in which an enzyme-labeled second antibody is used.

Using a cross-linking agent, the antigenic peptide is linked in advance to a carrier protein which is different from the one used in the immunization. A human FGF-8 partial peptide and a peptide having an animo acid sequence which is different from that of the partial peptide are linked to a carrier protein and used as control peptides. The peptide in a concentration of 1 to 50 $\mu$g/ml is distributed in 10 to 100 $\mu$l portions into each well of 96-well EIA plates and allowed to stand overnight at 4° C. to effect precoating. After blocking is effected with BSA solution or the like, a hybridoma culture supernatant or a purified antibody prepared in accordance with the following procedure (6) is used as a first antibody and distributed in 50 to 100 $\mu$l portions into each well of the EIA plates, and the reaction is carried out for 2 hours at room temperature or overnight at 4° C. After washing with PBS or a solution prepared by supplementing PBS with 0.05% Tween-20 (hereinafter referred to as "Tween-PBS"), 1 to 50 $\mu$g/ml solution of an anti-mouse or anti-rat immunoglobulin antibody labeled with biotin, an enzyme, a chemiluminescent substance, a radioactive compound or the like is used as a second antibody and distributed in 50 to 100 $\mu$l portions into each well of the EIA plate, and the reaction is carried out at room temperature for 1 to 2 hours. After thorough washing, each reaction corresponding to respective labeling substance of the second antibody is carried out, and a well which shows a specific bind to the human FGF-8 partial peptide is selected as a source of anti-FGF-8 monoclonal antibody.

(6) Preparation of monoclonal antibody

The hybridoma cells obtained in (4) capable of producing anti-FGF-8 monoclonal antibody are injected intraperitoneally into 8 to 10-week-old mice or nude mice treated with pristane (by intraperitoneal administration of 0.5 ml of 2,6,10,14-tetramethylpentadecane (pristane) followed by 3 to 10 days of rearing] at a dose of $2 \times 10^7$ to $5 \times 10^6$ cells per animal. The hybridoma causes an ascites tumor in 10 to 21 days. The ascitic fluid is collected from the mice, centrifuged (3,000 rpm, 5 minutes) to remove solid matter and, after salting out with 40 to 50% saturation ammonium sulfate, subjected to a caprylic acid precipitation method or passed through a DEAE-Sepharose column, a protein A column or a gel filtration column. Collected fractions of IgG or IgM are pooled to give a purified monoclonal antibody. The subclass of the antibody can be determined using a mouse monoclonal antibody typing kit or a rat monoclonal antibody typing kit. The amount of protein can be determined by the Lowry method or calculated based on the optical density at 280 nm.

(7) Confirmation of the specificity of the monoclonal antibody (Western blotting)

Bindability of the anti-FGF-8 monoclonal antibody selected in (5) with the FGF-8 protein is examined by Western blotting. A culture broth of a mouse breast cancer cell line SC-3 at the time of testosterone stimulation or FGF-8 protein in the culture broth or FGF-8 protein expressed in CHO cells is purified, fractionated by SDS-PAGE and then blotted on a nitrocellulose membrane or PVDF membrane. After blocking with BSA solution, reaction with a culture supernatant containing the anti-FGF-8 monoclonal antibody or 1 to 10 µg/ml of purified antibody is carried out at room temperature for 2 hours or overnight at 4° C. After washing with PBS or PBS-Tween, a 1 to 50 µg/ml solution of an anti-mouse or anti-rat immunoglobulin antibody labeled with biotin, an enzyme, a chemiluminescent substance, a radioactive compound or the like is used as a second antibody, and the reaction is carried out at room temperature for 1 to 2 hours. After thorough washing, each reaction corresponding to the respective labeling substance of the second antibody is carried out to confirm that the anti-FGF-8 monoclonal antibody can bind to the band which coincides with the molecular weight of the FGF-8 protein.

(8) Inhibition of FGF-B activity by the monoclonal antibody

The ability of the anti-FGF-8 monoclonal antibody selected in (5) to inhibit FGF activity is examined by a growth inhibition assay using a mouse breast cancer cell line SC-3 or a cell line derived from human prostatic cancer or breast cancer as the target cells. According to this method, the target cells are cultured in a medium containing FGF-8 (1 to 100 ng/ml) or testosterone, which is supplemented in advance with a culture supernatant containing the anti-FGF-8 monoclonal antibody or purified antibody serially diluted to a final concentration of 0.1 to 100 µg/ml. After 24 to 72 hours of culturing, the number of viable cells is measured using an MTT [3-(4,5-dimethyl-2-thiazonyl)-2,5-diphenyl-2H-tetrazolium bromide] solution or a cell counting kit, thereby confirming inhibition of FGF-8 activity by the anti-FGF-8 monoclonal antibody.

EXAMPLES

The present invention will now be illustrated in greater detail by way of Examples, but it should be understood that the invention is not construed as being limited thereto.

Example 1

(1) Preparation of immunogen

A peptide was synthesized by designing an amino acid sequence (SEQ ID NO:1) in which cysteine was added to the C-terminal of a partial amino acid sequence of human FGF-8, the 23 position residue to the 46 position residue counting from the N-terminal, in order to effect its binding with a carrier protein. The peptide synthesis was carried out using a multi-item simultaneous solid layer system automatic peptide synthesizer PSSM-8 (manufactured by Shimadzu Corp.). In order to improve antigenicity, a conjugate of the synthesized peptide with KLH (manufactured by Calbiochem Co.) was prepared and used as the immunogen. That is, KLH was dissolved in PBS to a concentration of 10 mg/ml, and ¹⁄₁₀ volume of 25 mg/ml MBS (Nakalai Tesque) was added dropwise to the KLH solution, followed by 30 minutes of reaction with stirring. Free MBS was removed by passing the reaction solution through a gel filtration column such as a Sephadex G-25 column (Pharmacia) or the like which has been equilibrated in advance with PBS, thereby obtaining 2.5 mg of a KLH-MBS conjugate. This was further mixed with 1 mg of the peptide dissolved in 0.1 M sodium phosphate buffer (pH 7.0), and the mixture was stirred at room temperature for 3 hours to effect the reaction. After the reaction, the reaction solution was dialyzed against PBS-0.5 M NaCl and used as the immunogen.

(2) Immunization of animals and preparation of antibody-producing cells

A 100 µg portion of the peptide-KLH conjugate prepared by the method described in Example 1 (1) was administered together with 2 mg of aluminum gel and $1 \times 10^9$ cells of pertussis vaccine (manufactured by Chiba Serum Institute) to mice of 5 weeks of age (Balb/c). Starting 2 weeks after the administration, 100 µg of the peptide-KLH conjugate was administered once a week in total of 4 times. A blood sample was collected from the venous plexus of the fundus of the eye, antibody titer of the serum derived from the sample blood was examined by an enzyme immunoassay which will be described in Example 1 (3), and the spleen was excised from a mouse showing sufficient antibody titer after 3 days of the final immunization. The spleen was cut to pieces in MEM medium (manufactured by Nissui Pharmaceutical), loosened using a pair of forceps and then subjected to 5 minutes of centrifugation at 1,200 rpm. Thereafter, the supernatant was discarded, the obtained precipitate was treated with Tris-ammonium chloride buffer (pH 7.65) for 1 to 2 minutes to remove erythrocytes, and then the remaining cells were washed three times with MEM medium and used for cell fusion.

(3) Enzyme immunoassay

A conjugate obtained by cross-linking the human FGF-8 partial peptide shown in (SEQ ID NO:1) with thyroglobulin in the following manner was used as the antigen for the assay. That is, 1 mg of the peptide was dissolved in 0.1 M ammonium acetate buffer and the solution was adjusted to 1 ml by adding 5 mg of THY which has been dissolved in advance in the same buffer. To this, while stirring, was added dropwise 540 µl of 0.02 M glutaraldehyde, followed by 5 hours of stirring at room temperature to effect the reaction. After the reaction, the reaction solution was dialyzed overnight against PBS and used as the antigen. A conjugate obtained in the same manner by cross-linking the peptide shown in (SEQ ID NO:2) with THY was used as a reference antigen. A 10 µg/ml solution of the prepared conjugate was distributed in 50 µl portions in wells of a 96-well plate for EIA (manufactured by Greiner), and the plate was allowed to stand overnight at 4° C. to effect coating. After washing, 1% BSA-PBS was distributed in 100 µl portions into wells of the plate which was subsequently subjected to 1 hour of reaction at room temperature to block the remaining active groups. The 1% BSA-PBS was then discarded, and a hybridoma culture supernatant or an immunized mouse antiserum was distributed in 50 μl portions into wells of the plate, subsequently carrying out 2 hours of reaction. After washing with Tween-PBS, a peroxidase-labeled rabbit anti-mouse immunoglobulin (manufactured by DAKO) was distributed in 50 μl portions into wells of the plate to carry out 1 hour of reaction at room temperature, the plate was again washed with Tween-PBS, and then color development was effected using an ABTS substrate [2,2-azinobis(3-ethylbenzothiazole-6-sulfonic acid) ammonium] solution and absorbance at $OD_{415}$ was measured (NJ 2001; Japan Intermed).

(4) Preparation of mouse myeloma cells

The 8-azaguanine-resistant mouse myeloma cell line P3-U1 was cultured in the normal medium and not less than $2 \times 10^7$ cells were thereby secured at the time of cell fusion and submitted for cell fusion as a parent line.

(5) Preparation of hybridoma

The mouse splenocytes obtained in Example 1 (2) and the myeloma cells obtained in Example 1 (4) were mixed in a ratio of 10:1, and the mixture was centrifuged (1,200 rpm, 5 minutes). The supernatant was discarded, and the precipitated cells were thoroughly loosened. A solution composed of a mixture of 2 g of polyethylene glycol-1,000 (PEG-1,000), 2 ml of MEM medium and 0.7 ml of dimethyl sulfoxide was added to the cells with stirring at 37° C. in an amount of 0.2 to 1 ml per $10^8$ mouse splenocytes, followed by the addition of several 1 to 2 ml portions of MEM medium at 1 to 2 minute intervals. Thereafter, the total volume was made 50 ml by addition of MEM medium. After centrifugation (900 rpm, 5 minutes), the supernatant was discarded, and the cells were gently loosened and then gently suspended in 100 ml of HAT medium by repeated drawing up into and discharging from a graduated pipette. The suspension was distributed in 100 μl portions into wells of a 96-well culture plate, and incubation was performed in a 5% $CO_2$ incubator at 37° C. for 10 to 14 days. Each culture supernatant was examined by the enzyme immunoassay described in Example 1 (3) to select wells which showed specific reaction with the FGF-8 peptide. Using the selected wells, cloning was repeated twice using HT medium and the normal medium, respectively, thereby establishing hybridoma cell lines capable of producing the anti-FGF-8 monoclonal antibody. The monoclonal antibody KM 1334 shown in FIG. 1 is an example of these hybridoma cell lines. Hybridoma KM 1334 was deposited on Mar. 7, 1996, at the National Institute of Bioscience and Human-Technology, Agency of Industrial Science and Technology, (1-3, Higashi 1-chome, Tsukuba-shi, Ibaraki, Japan), and has been assigned the designation FERM BP-5451. In this connection, its antibody class was IgG1 determined by an enzyme immunoassay using a subclass typing kit.

(6) Purification of monoclonal antibody

The hybridoma cell line obtained in Example 1 (3) was intraperitoneally administered to pristane-treated female nude mice (Balb/c) of 8 weeks of age at a dose of 5 to $20 \times 10^6$ cells per animal. The hybridoma caused ascites tumor in 10 to 21 days. The ascitic fluid was collected from each ascitic fluid-carrying mouse (1 to 8 ml per animal), centrifuged (3,000 rpm, 5 minutes) to remove solid matter and then purified by the caprylic acid precipitation method (Antibodies—A Laboratory Manual, Cold Spring Harbor Laboratory, 1988) to obtain purified monoclonal antibody.

Example 2

Figure 2:
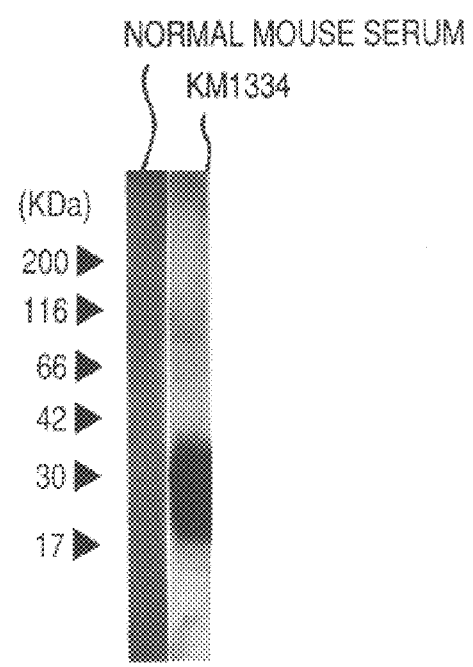
FIG. 2 shows the reactivity of anti-FGF-8 monoclonal antibody KM 1334 with purified FGF-8 protein in Western blotting.

(1) Examination of the specificity of the monoclonal antibody by Western blotting The FGF-8 protein purified from a culture broth of the mouse breast cancer cell line SC-3 at the time of testosterone stimulation was fractionated by SDS-PAGE in an amount of 0.1 μg per lane and then blotted on a PVDF film in the usual way. After blocking with 1% BSA-PBS, reaction with the anti-FGF-8 monoclonal antibody KM 1334 (10 μg/ml) or normal mouse serum used as a control antibody (×500) was carried out at room temperature for 2 hours or overnight at 4° C. After thorough washing with Tween-PBS, reaction with a peroxidase-labeled anti-mouse immunoglobulin antibody (manufactured by DAKO) was carried out at room temperature for 1 hour. After thorough washing with Tween-PBS, reaction with ECL (manufactured by Amersham) reagent was carried out for 1 minute, excess reagent was removed and then detection was effected by sensitizing the treated film for about 10 seconds to 2 minutes. As shown in FIG. 2, KM 1334 bound to FGF-8. Although FGF-8 has a theoretical value of 22 K dalton, it was observed as a band of around 30 K dalton due to addition of sugar chains and the like.

(2) Examination on the inhibition of FGF-8 activity by the monoclonal antibody

Figure 3:
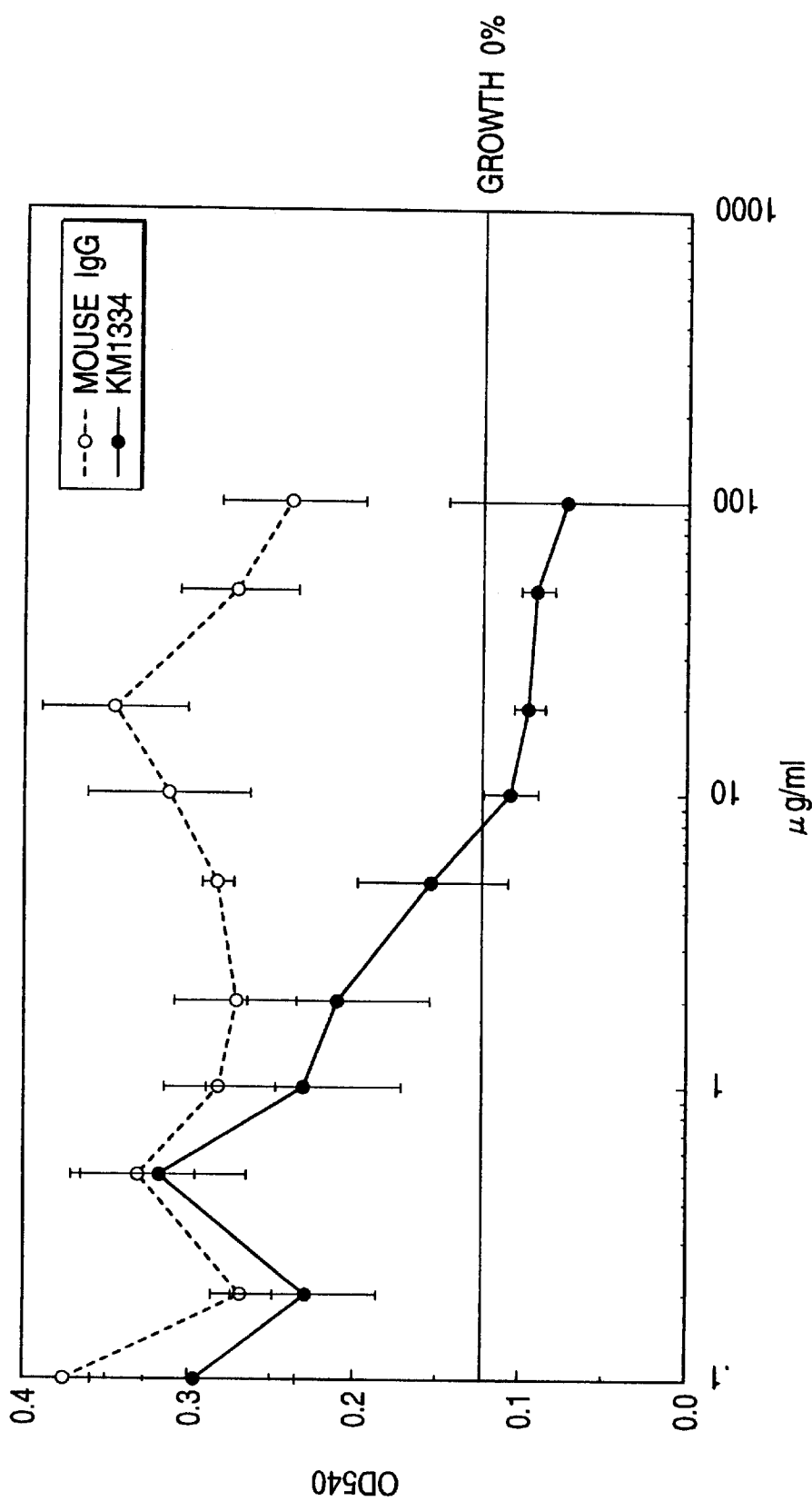
FIG. 3 shows the effect of anti-FGF-8 monoclonal antibody KM 1334 in inhibiting the activity of FGF-8. In the drawing, the line of growth at 0% indicates a value when neither the growth factor nor antibody were added. The dotted line indicates activity inhibition by purified mouse IgG used as a control antibody, and the solid line by anti-FGF-8 monoclonal antibody KM 1334.
Figure 4:
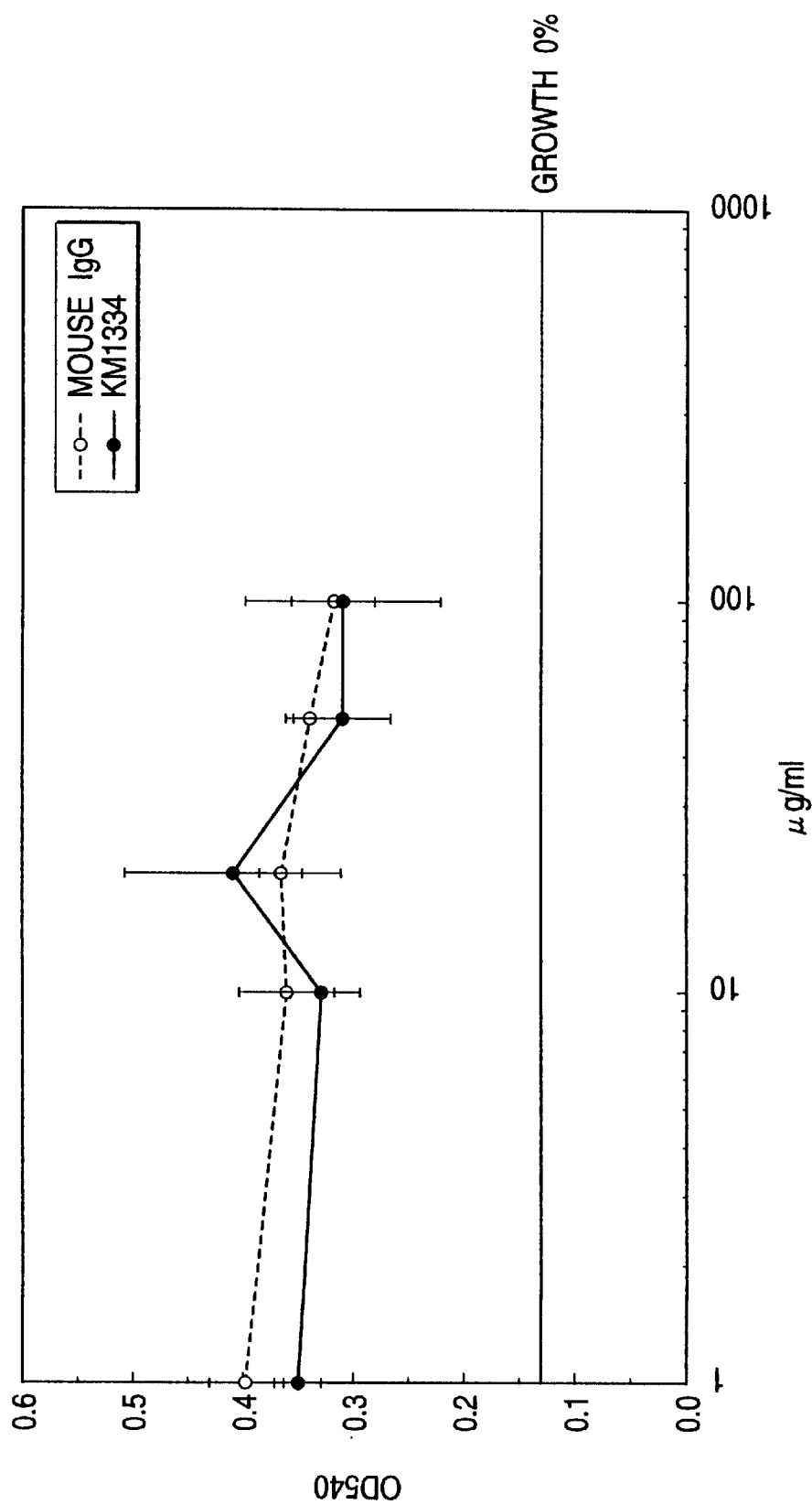
FIG. 4 shows the effect of anti-FGF-8 monoclonal antibody KM 1334 in inhibiting the activity of bFGF. In the drawing, the line of growth at 0% indicates a value when neither the growth factor nor antibody were added. The dotted line indicates activity inhibition by purified mouse IgG used as a control antibody, and the solid line by anti-FGF-8 monoclonal antibody KM 1334.

The ability of the anti-FGF-8 monoclonal antibody to inhibit FGF-8 activity was examined by a growth inhibition assay using the mouse breast cancer cell line SC-3 as the target cells. The SC-3 cells were cultured in a medium containing FGF-8 (50 ng/ml), testosterone (10 nM, manufactured by Nakalai Tesque) or basic fibroblast growth factor (hereinafter referred to as "bFGF" (1 ng/ml, manufactured by Pepro Tech Inc.)). In this case, the medium was supplemented in advance with the anti-FGF-8 monoclonal antibody KM 1334 serially diluted to a final concentration of 0.1 to 100 μg/ml. As a control antibody, purified mouse IgG (manufactured by Sigma) was used. After 72 hours of culturing, the number of viable cells was measured by an MTT method. That is, a 5 mg/ml solution of MTT [3-(4,5-dimethyl-2-thiazonyl)-2,5-diphenyl-2H-tetrazolium bromide] in PBS was distributed in 10 μl portions into wells of culture plate and incubated at 37° C. for 4 to 5 hours, 0.04 N HCl-isopropanol was distributed in 150 μl portions into the resulting wells and then the plate was shaken at 37° C. for 1 to 2 hours. The formed pigment was then solubilized and its absorbance at $OD_{540}$ nm was measured. Results of inhibition against activity of FGF-8, bFGF and testosterone are shown in FIGS. 3, 4 and 5, respectively. As shown in FIG. 3, KM 1334 inhibited the growth of SC-3 cells by FGF-8 in a dose-dependent manner, but, as shown in FIG. 4, KM 1334 did not show dose-dependent inhibition of SC-3 cells by bFGF. In consequence, it was confirmed that KM 1334 inhibits the FGF-B activity specifically. In addition, as shown in FIG. 5, KM 1334 partially inhibited the growth of SC-3 cells by testosterone, but not completely at an antibody concentration of 100 μg/ml.

The present invention provides a monoclonal antibody which specifically binds to FGF-8 and inhibits FGF-8 activity. The monoclonal antibody of the present invention is useful in analyzing the role and biological function of FGF-8 in tumor cells and can be used to diagnose prostatic cancer, breast cancer and the like by immunological detection.

While the invention has been described in detail and with reference to specific embodiments thereof, it will be apparent to one skilled in the art that various changes and modifications can be made therein without departing from the spirit and scope thereof.

This application is based on application No. Hei 8-81754 filed in Japan, the content of which is incorporated hereinto by reference.

What is claimed is:

1. A monoclonal antibody which specifically binds to SEQ ID NO:1, found in the N terminal region of human fibroblast growth factor-8, and which inhibits activity of fibroblast growth factor-8.

2. A monoclonal antibody of the IgG1 subclass produced by hybridoma FERM BP-5451.

3. A hybridoma FERM BP-5451 which produces a monoclonal antibody specifically binding to fibroblast growth factor-8.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 25 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:1:

Gln Val Thr Val Gln Ser Ser Pro Asn Phe Thr Gln His Val Arg Glu
1               5                  10                  15

Gln Ser Leu Val Thr Asp Gln Leu Cys
            20                  25

(2) INFORMATION FOR SEQ ID NO:2:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:2:

Cys Ala Thr Ala Ala Asp Gln Glu Leu Asn Pro Glu Gly Asp Gly
1               5                  10                  15